US008703724B2

(12) United States Patent
Kratz

(10) Patent No.: US 8,703,724 B2
(45) Date of Patent: Apr. 22, 2014

(54) LOW-VISCOUS ANTHRACYCLINE FORMULATION

(75) Inventor: Felix Kratz, Ihringen (DE)

(73) Assignee: KTB Tumorforschungs GmbH, Freiburg (DE)

(*) Notice: Subject to any disclaimer, the term of this patent is extended or adjusted under 35 U.S.C. 154(b) by 654 days.

(21) Appl. No.: 12/619,161

(22) Filed: Nov. 16, 2009

(65) Prior Publication Data

US 2010/0152273 A1 Jun. 17, 2010

Related U.S. Application Data

(63) Continuation of application No. PCT/EP2008/003969, filed on May 16, 2008.

(30) Foreign Application Priority Data

May 16, 2007 (EP) .................................. 07009865

(51) Int. Cl.
*A61K 31/7032* (2006.01)
(52) U.S. Cl.
USPC .......................................................... 514/34
(58) Field of Classification Search
None
See application file for complete search history.

(56) References Cited

U.S. PATENT DOCUMENTS

| 4,043,997 | A | | 8/1977 | Schroeder |
| 4,840,938 | A | * | 6/1989 | Gatti et al. ...................... 514/34 |
| 5,091,373 | A | | 2/1992 | Gatti et al. |
| 5,157,044 | A | | 10/1992 | Schoenwald et al. |
| 5,262,526 | A | | 11/1993 | Sasamoto et al. |
| 5,612,474 | A | | 3/1997 | Patel |
| 5,780,446 | A | | 7/1998 | Ramu |
| 5,919,815 | A | | 7/1999 | Bradley et al. |
| 6,267,964 | B1 | | 7/2001 | Nygren et al. |
| 6,310,039 | B1 | | 10/2001 | Kratz |

FOREIGN PATENT DOCUMENTS

| CA | 2058220 A1 | 6/1992 |
| CA | 2303299 A1 | 3/1999 |
| DE | 19636889 A1 | 3/1998 |
| EP | 0 624 377 | 11/1994 |
| EP | 0 665 020 A2 * | 8/1995 |
| EP | 1054039 A1 | 11/2000 |
| EP | 1 435 231 | 7/2004 |
| JP | 07076515 A * | 3/1995 |
| WO | WO-8803412 A1 | 5/1988 |
| WO | WO 91/05806 | 5/1991 |
| WO | WO 96/39183 | 12/1996 |
| WO | WO-9729759 A1 | 8/1997 |
| WO | WO 98/08859 | 3/1998 |
| WO | WO 98/10794 | 3/1998 |
| WO | WO-9914226 A2 | 3/1999 |
| WO | WO 00/02050 | 1/2000 |
| WO | WO 03/022247 | 3/2003 |

OTHER PUBLICATIONS

Kratz et al. Human & Experimental Toxicology, Jan. 2007, vol. 26, pp. 19-35.*
Lebrecht et al. Int. J. Cancer, 2006, vol. 120, pp. 927-934.*
Andresen et al., "Advanced strategies in liposomal cancer therapy: problems and prospects of active and tumor specific drug release," Progress in Lipid Research 44:68-97 (2005).
Hayakawa, "Visible Absorption and Proton Nuclear Magnetic Resonance Studies on the Self-Association of Doxorubicin in Aqueous Solution," Chem Pharm Bull 39:1009-1012 (1991).
Hudson et al., "Cellular delivery of hammerhead ribozymes conjugated to a transferrin receptor antibody," Int'l. J. Pharm. 182:49-58 (1999).
Kratz et al., "Prodrugs of anthracyclines in cancer chemotherapy," Curr. Med. Chem. 13(5):477-523 (2006).
Kratz and Beyer, "Serum proteins as drug carriers of anticancer agents: a review," Drug Delivery 5:281-299 (1998).
Kratz, et al, "Preparation, characterization and in vitro efficacy of albumin conjugates of doxorubicin," Biological & Pharm. Bulletin 21:56-61 (1998).
Majumdar et al., "Membrane transporter/receptor-targeted prodrug design: strategies for human and veterinary drug development," Advanced Drug Delivery Reviews 56:1437-1452 (2004).
Makrides et al., "Extended in vivo half-life of human soluble complement receptor type 1 fused to a serum albumin-binding receptor," J. Pharmacol Exp. Ther. 277:534-542 (1996).
Minks et al., "Atomic mutations at the single tryptophan residue of human recombinant annexin V: effects on structure, stability, and activity," Biochemistry 38: 10649-10659 (1999).
Monneret, "Recent developments in the field of antitumour anthracyclines," Eur. J. Med. Chem. 36(6):483-493 (2001).
Nagy et al., "High yield conversion of doxorubicin to 2-pyrrolinodoxorubicin, an analog 500-1000 times more potent: structure-activity relationship of daunosamine-modified derivatives of doxorubicin," Proc. Natl. Acad. Sci. 93:2464-2469 (1996).
Penichet et al., "An antibody-avidin fusion protein specific for the transferrin receptor serves as a delivery vehicle for effective brain targeting: initial applications in anti-HIV antisense drug delivery to the brain," J. Immun. 163:4421-4426 (1999).
Takahashi et al., "Design and synthesis of a water-soluble taxol analogue: taxol-sialyl conjugate," Bioorg. Med. Chem. Lett. 8:113-116 (1998).
Trouet et al., "A covalent linkage between daunorubicin and proteins that is stable in serum and reversible by lysosomal hydrolases, as required for a lysosomotropic drug-carrier conjugate: in vitro and in vivo studies", Proc. Nat. Acad. Sci. 79:626-629 (1982).
Ajaj et al., "In vitro and in vivo study of an albumin-binding prodrug of doxorubicin that is cleaved by cathespin B," Cancer Chemother Pharmacol, 64:413-418 (2009).
Beyer et al., "Synthesis of New Bifunctional Maleimide Compounds for the Preparation of Chemoimmunoconjugates", *Monatshefte für Chemie* 128, pp. 91-102 (1997), Austria.

(Continued)

*Primary Examiner* — James D Anderson
(74) *Attorney, Agent, or Firm* — Rothwell, Figg, Ernst & Manbeck, P.C.

(57) ABSTRACT

The present invention relates to formulations comprising an anthracycline compound and an aromatic or heterocyclic compound.

13 Claims, No Drawings

(56) References Cited

OTHER PUBLICATIONS

Firestone et al., "Synthesis and antitumor activity of the immunoconjugate BR96-Dox," J. Controlled Release, 39:251-259 (1996).

Graeser et al., "Synthesis and biological evaluation of an albumin-binding prodrug of doxorubicin that is cleaved by prostrate-specific antigen (PSA) in a PSA-positive orthotopic prostate carcinoma model (LNCaP)," Int. J. Cancer, 122:1145-1154 (2008).

Kruger et al., "Synthesis and Stability of Four Maleimide Derivatives of the Anticancer Drug Doxorubicin for the Preparation of Chemoimmunoconjugates", Chem. Pharm. Bull 45(2) pp. 399-401 (1997).

Poster published in Annals in Oncology, Supplement, NCI/EOTCR Amsterdam, Nov. 7-10, (2000).

Trail et al., "Effect of Linker Variation on the Stability, Potency, and Efficacy of Carcinoma-reactive BR64-Doxorubicin Immunoconjugates," Cancer Res., 57:100-105 (1997).

Warnecke et al., "Maleimide-oligo (ethylene glycol) Derivatives of Camptothecin as Albumin-Binding Prodrugs: Synthesis and Antitumor Efficacy," Bioconjugate Chem., 14:377-387 (2003).

Warnecke et al., "Synthesis and Biological Activity of Water-Soluble Maleimide Derivatives of the Anticancer Drug Carboplatin Designed as Albumin-Binding Prodrugs," Bioconjugate Chem., 15:1349-1359 (2004).

Willner et al. (6-Maleimidocaproyl) hydrazone of Doxorubicin-A New Derivative for the Preparation of Immunoconjugates of Doxorubicin, Bioconjugate Chem. 4, 521-527 (1993).

* cited by examiner

LOW-VISCOUS ANTHRACYCLINE FORMULATION

This application is a continuation of International Application PCT/EP2008/003969, filed May 16, 2008, which claims the benefit of European Application 07 009 865.2, filed May 16, 2007. The entire disclosures of each of these referenced applications are incorporated by reference herein.

The present invention relates to formulations comprising an anthracycline compound and an aromatic or heterocyclic compound.

Anthracyclines such as doxorubicin, daunorubicin, epirubicin, idarubicin, pirarubicin, zorubicin, aclarubicin or caminomycin are used in the treatment of malignant diseases. Due to narrow therapeutic window of these agent, several anthracycline derivatives (Monneret, C. *Eur. J. Med. Chem.*, 2001, 36, 483-493) and prodrugs (Kratz, F.; Warnecke, A.; Schmid, B.; Chung, D. E.; Gitzel, M. *Curr. Med. Chem.* 2006, 13, 477) have been developed and first candidates are undergoing clinical studies. A prerequisite for such studies is the availability of a sterile formulation of the respective anthracycline derivative. Due to the structure of anthracyclines, they can form physical aggregates and self-associate in solution which is dependent on the concentration, the salt concentration, the temperature and the pH value (Hayakawa, E. et al., *Chem. Pharm. Bull.* 1991, 39, 1009-1012). Physical aggregation can lead to gel formation and viscous solutions which cannot be sterile-filtered.

Anthracyclines form aggregates in aqueous solution ("stacking effect"). For the most commonly used anthracyclines doxorubicin, daunorubicin, epirubicin and idarubicin, the stacking effect can be reduced by dissolving the anthracycline at an acidic pH value and a low salt concentration so that the solution can be sterile-filtered. For certain anthracycline derivatives and prodrugs these conditions are not sufficient to reduce the viscosity of the resulting solution, or they are not applicable due to stability issues. The extent of aggregation will depend on the chemical modification of the anthracycline. In acid-sensitive prodrugs the pH cannot be too acidic in order to prevent cleavage. In addition, with acid-sensitive prodrugs or labile anthracycline derivatives it is often desirable to prepare solutions at temperatures below room temperature before sterile filtration which in turn increases the viscosity of the solution.

Therefore, it was an object of the invention to provide anthracycline formulations having reduced viscosity, in particular, to allow sterile filtration of such formulations.

According to the invention said object is achieved by a formulation comprising an anthracycline compound and an aromatic or heterocyclic compound.

The present invention relates to a procedure that reduces aggregation and/or viscosity of solutions of anthracycline compounds and, in particular, of anthracycline derivatives, making them amenable to sterile filtration.

In the present invention it was found that the addition of aromatic or heterocyclic compounds can prevent or reduce aggregation of anthracycline compounds such as anthracycline derivatives and/or prodrugs, thus decreasing the viscosity of the respective aqueous solution. By the addition of aromatic or heterocyclic compounds according to the invention it is possible to keep the viscosities of solutions containing anthracycline derivatives low enough to allow sterile filtration. Thereby the formulations of the invention still have sufficiently low viscosity, even at low temperatures, in particular, at temperatures <10° C., more preferably <5° C. This is especially advantageous because solutions containing anthracycline compounds often show only low stability at higher temperatures.

Sterile filtration, as used herein, in particular, refers to filtration through a 1 μm filter and preferably through a 0.2 μm or smaller filter. The viscosity of the formulations of the invention is preferably ≤1000 mPa·s, more preferably ≤100 mPa·s, especially ≤50 mPa·s, even more preferably ≤5 mPa·s, and in particular ≤2 mPa·s at a temperature of 18° C., in particular, at 10° C., preferably at 5° C. and more preferably at 3° C.

According to the invention the formulations comprise an aromatic or heterocyclic compound. Heterocyclic compounds are any compounds which comprise a cycle in their structure, wherein the cycle contains at least one heteroatom besides carbon atoms, in particular, a heteroatom selected from O, N, S or P, in particular, O and/or N. A heterocycle preferably contains 1 to 5, more preferably 1 to 3, and most preferably 1 to 2 heteroatoms.

Aromatic compounds are any compounds which comprise an aromatic moiety. The aromatic moiety may be formed of a cycle containing only carbon atoms or of a cycle which also contains heteroatoms, in particular, selected from O, N, S and P, preferably O and N.

The formulations of the invention preferably comprise an anthracycline compound and an aromatic compound.

The aromatic or heterocyclic compound of the present invention can be mono- or polycyclic. Preferred monocycles are benzoic acid and its derivatives such as hydroxybenzoic acid, alkylhydroxybenzoic acid (alkyl=methyl, ethyl, propyl, butyl), benzylalcohol and its derivatives, and niacin, in particular, nicotinic acid and/or nicotinic acid amide, and its derivatives.

Further preferred aromatic compounds of the present invention are amino acids or N-substituted amino acids, e.g. N-acetyl substituted amino acids. Especially preferred amino acids are tyrosine, phenylalanine, histidine or tryptophane. Most preferred N-substituted amino acids are D-N-acetyltryptophane, L-N-acetyltryptophane, or D,L-N-acetyltryptophane.

The formulations of the invention further comprise an anthracycline compound, preferably an anthracycline derivative. In a preferred embodiment, the anthracycline derivative is derived from doxorubicin, daunorubicin, epirubicin, idarubicin, pirarubicin, zorubicin, aclarubicin or caminomycin. The anthracycline derivatives, in particular, contain a binding moiety which allows binding of the anthracycline to a biomolecule and, in particular, to a protein. Thus, preferred anthracycline derivatives contain a maleinimide, a halogen acetate amide, a halogen acetate, a pyridyldithio, a N-hydroxysuccinimide ester or an isothiocyanate group, most preferably a maleinimide group. Further preferred are anthracycline derivatives which are anthracycline hydrazone derivatives.

Especially preferred anthracycline derivatives have the general formula

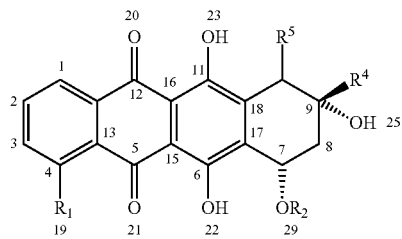

wherein
$R_1$ is $OCH_3$, $OC_2H_5$, H or OH, $R_2$ is a glycoside, $R_4$ and $R_5$ independently are H, OH, $C_1$-$C_4$ alkyl, in particular, $C_2H_5$, $OC_1$-$C_4$ alkyl or $C(CH_2R_3)=N-NH-CO-X-Y$, wherein $R_3$ is H or OH, X is a linking group, in particular, $-(CH_2)_n-$, $-(CH_2)_n-C_6H_4-$ or $-C_6H_4-$, wherein n=1-12, and Y is a binding group, in particular, a maleinimide group, a halogen acetate amide group, a halogen acetate group, a pyridyldithio group, an N-hydroxysuccinimide ester group, isothiocyanate group, a disulfide group, a vinylcarbonyl group, an aziridine group or an acetylene group, with the proviso that at least one of $R_4$ and $R_5$ is $C(CH_2R_3)=N-NH-CO-X-Y$.

In an embodiment of the present invention the anthracycline derivative has the general formula

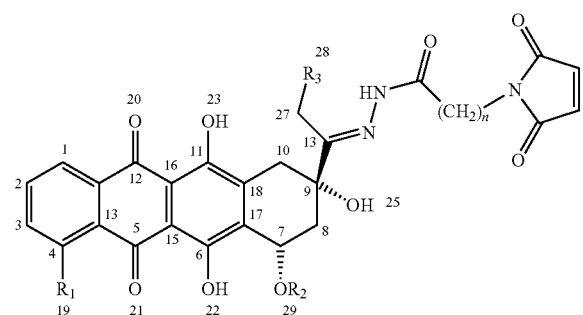

wherein $R_1$ is $OCH_3$, H, OH or $OC_2H_5$;

$R_2$ is a glycoside; in particular, 3-amino-2,3,6-trideoxy-alpha-L-lyxoheteropyranosyl, 3-amino-2,3,6-trideoxy-4-O-(tetrahydro-2H-pyran-3-yl)-alpha-L-lyxo-hexapyranosyl or 3-amino-2,3,6-trideoxy-4-O-(4-O-tetrahydro-2H-pyran-3-yl-tetrahydro-2H-pyran-3-yl)-alpha-L-lyxo-hexapyranosyl;

$R_3$ is H, OH or $OCH_3$, and n is an integer from 1 to 12 and, in particular, doxorubicin:

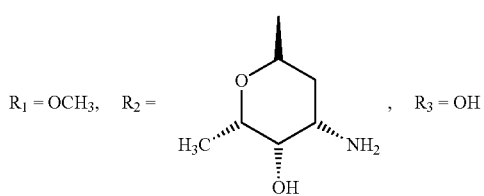

daunorubicin:

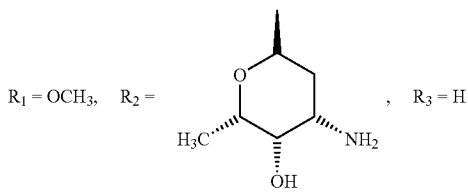

epirubicin:

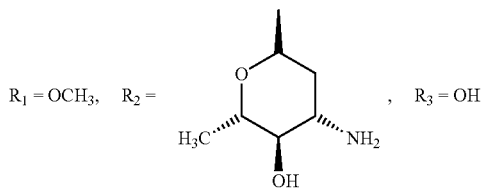

idarubicin:

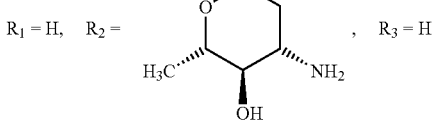

and n=1-12.

In a specific embodiment the anthracycline is doxorubicin and n=5, i.e. the anthracycline derivative is the 6-maleimidocaproylhyrazone derivative of doxorubicin.

In a further embodiment of the present invention the anthracycline derivative has the general formula

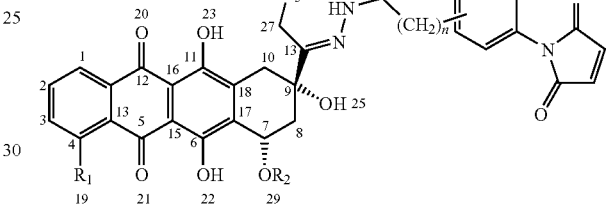

wherein $R_1$ is $OCH_3$, H, OH or $OC_2H_5$;

$R_2$ is a glycoside, in particular, 3-amino-2,3,6-trideoxy-alpha-L-lyxo-heteropyranosyl, 3-amino-2,3,6-trideoxy-4-O-(tetrahydro-2H-pyran-3-yl)-alpha-L-lyxo-hexapyranosyl or 3-amino-2,3,6-trideoxy-4-O-(4-O-tetrahydro-2H-pyran-3-yl-tetrahydro-2H-pyran-3-yl)-alpha-L-lyxo-hexapyranosyl;

$R_3$ is H, OH or $OCH_3$, and n is an integer from 1 to 12 and, in particular, doxorubicin:

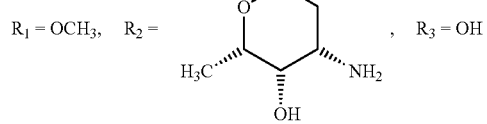

daunorubicin:

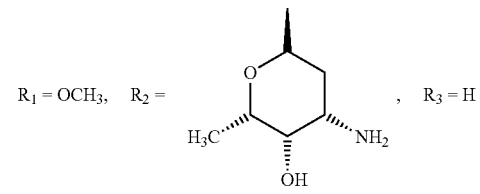

epirubicin:

$R_1 = OCH_3$, $R_2 =$ 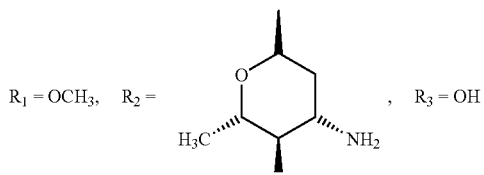, $R_3 = OH$ idarubicin:

$R_1 = H$, $R_2 =$ 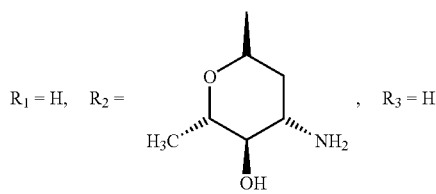, $R_3 = H$ and n=1-12.

In a specific embodiment the anthracycline is doxorubicin and n=1, i.e. the anthracycline is the 6-phenylacetylhydrazone derivative of doxorubicin.

In a further embodiment of the present invention the anthracycline derivative has the general formula

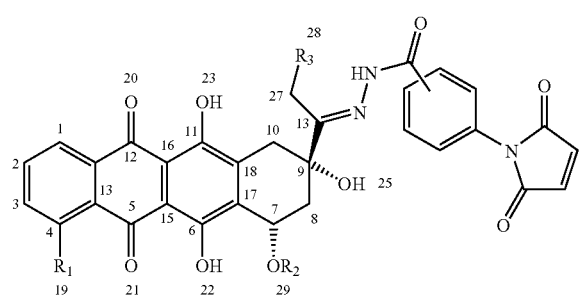

wherein $R_1$ is $OCH_3$, H, OH or $OC_2H_5$;

$R_2$ is a glycoside, in particular, 3-amino-2,3,6-trideoxy-alpha-L-lyxo-heteropyranosyl, 3-amino-2,3,6-trideoxy-4-O-(tetrahydro-2H-pyran-3-yl)-alpha-L-lyxo-hexapyranosyl or 3-amino-2,3,6-trideoxy-4-O-(4-O-tetrahydro-2H-pyran-3-yl-tetrahydro-2H-pyran-3-yl)-alpha-L-lyxo-hexapyranosyl;

$R_3$ is H, OH or $OCH_3$, and doxorubicin:

$R_1 = OCH_3$, $R_2 =$ 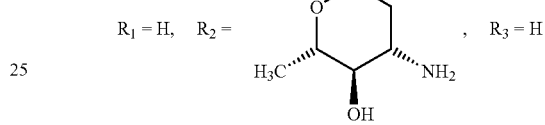, $R_3 = OH$ daunorubicin:

$R_1 = OCH_3$, $R_2 =$ 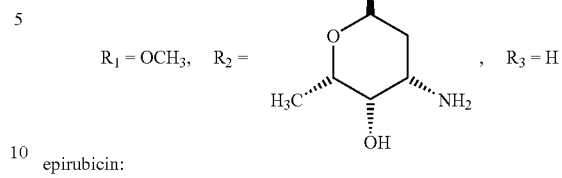, $R_3 = H$ epirubicin:

$R_1 = OCH_3$, $R_2 =$ 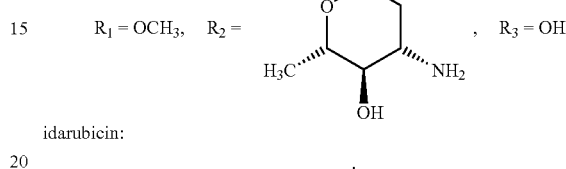, $R_3 = OH$ idarubicin:

$R_1 = H$, $R_2 =$ , $R_3 = H$

In a specific embodiment the anthracycline is doxorubicin and the maleimide derivative is 3- or 4-maleimidobenzoic acid hydrazide, i.e. the anthracycline derivative is the 3- or 4-maleimidobenzoylhyrazone derivative of doxorubicin.

The formulation according to the invention preferably is an aqueous formulation, in particular, a formulation containing at least 10 wt.-%, more preferably at least 50 wt.-% water. Especially preferably, the formulation is a pharmaceutical composition.

The ratio between the anthracycline compound, in particular, the anthracycline derivative, and the aromatic or heterocyclic compound can vary according to the present invention. A preferred ratio between the anthracycline derivative and the aromatic or heterocyclic compound is in the range of approximately 0.5 to 10, in particular, from 0.8 to 5 (referred to weight).

The amount of anthracycline compound in the formulation is preferably from 0.1 wt. % to 10 wt. %, more preferably from 0.5 wt. % to 5 wt. % based on the total weight of the formulation.

The amount of aromatic or heterocyclic, in particular, aromatic compound is preferably from 0.1 wt. % to 10 wt. %, in particular, from 0.2 wt. % to 5 wt. %.

Typically, the aromatic or heterocyclic compound of the present invention is added to water or a buffer before adding the anthracycline derivative, but if desired the aromatic or heterocyclic compound can also be added after the anthracycline derivative.

The buffer solutions are made of common salts for preparing buffers such as sodium or potassium phosphate, carbonate, sulphate, acetate, or citrate.

The formulations may contain in addition a pharmaceutical solvent or solubilizer such as tert.-butanol, 1-butanol, 2-butanol, ethanol, 1-propanol, isopropanol, 1,2-propylene glycol, glycerol, macrogols, polyethylene glycols or polyethylene oxides, Tween, Cremophor or polyvinylpyrrolidone. Furthermore, the formulations can contain an excipient such as sucrose, mannitol, or lactose. For stability reasons, the buffer—dependent on its composition—can be pre-cooled to a temperature of −20° C.

The pH value of the buffer is typically in the range of pH 4.0-9.0, preferably in the range pH 5.0-8.0.

In a specific embodiment of the present invention the 6-maleimidocaproylhyrazone derivative of doxorubicin is formulated in the presence of D,L-N-acetyltryptophane. The molar ratio of the 6-maleimidocaproylhyrazone derivative of doxorubicin (DOXO-EMCH) to D,L-N-acetyltryptophane is in the range of approximately 0.5 to 2.0. For preparing the pharmaceutical composition, the 6-maleimidocaproylhyrazone derivative of doxorubicin is added to pre-cooled water or a pre-cooled sodium phosphate buffer (pH 5.0-6.5) containing sucrose or mannitol as an excipient and D,L-N-acetyltryptophane as the heterocyclic compound of the present invention that reduces the viscosity of the solution and makes sterile filtration possible. For stability reasons, the buffer is pre-cooled to a temperature in the range of +6 to −5° C. If D,L-N-acetyltryptophane is not present, sterile filtration is not possible due to the high viscosity of the DOXO-EMCH solution. For sterile filtration commercially available cartridges with a 0.2 μm filter are used. After sterile filtration the DOXO-EMCH solution is filled into vials and lyophilized.

In another specific embodiment of the present invention the 6-maleimidocaproylhyrazone derivative of doxorubicin is formulated in the presence of D,L-N-acetyltryptophane and tert.-butanol. The ratio of the 6-maleimidocaproylhyrazone derivative of doxorubicin (DOXO-EMCH) to D,L-N-acetyltryptophane is in the range of approximately 0.5-2.0. For preparing the pharmaceutical composition, the 6-maleimidocaproylhyrazone derivative of doxorubicin is added to a mixture of pre-cooled sodium phosphate buffer (pH 5.0-6.5) and tert.-butanol containing sucrose or mannitol as an excipient and D,L-N-acetyltryptophane as the heterocyclic compound of the present invention that reduces the viscosity of the solution and makes sterile-filtration possible. The content of tert.-butanol in the buffer mixture is in the range of approximately 20-80%, in a preferred embodiment it is 50%. For stability reasons, the buffer mixture is pre-cooled to a temperature in the range of +6 to −15° C. If D,L-N-acetyltryptophane is not present, sterile-filtration is not possible due to the high viscosity of the DOXO-EMCH solution. For sterile-filtration commercially available cartridges with a 0.2 μm filter are used. After sterile-filtration the DOXO-EMCH solution is filled into to vials and lyophilized.

The present invention is illustrated in the following examples without any limitation thereto.

Example 1

To a jacketed vessel fitted with an overhead stirrer are added 4767 mL of a sterile buffer containing 10 mM sodium phosphate, 0.6% D,L-N-acetyltryptophane, and 5% D-sucrose with a pH value of 6.0. The buffer is stirred and with the aid of a circulating brine solution the temperature of the buffer is adjusted to +5° C. To the pre-cooled buffer are added 96.458 g of the 6-maleimidocaproyl hydrazone derivative of doxorubicin hydrochloride (DOXO-EMCH HCl). DOXO-EMCH HCl is dissolved by stirring and sterile-filtered through a Acropak 500 filter (0.8/0.2 μm) into a second jacketed vessel set at −3° C. Under stirring 50 mL vials are filled immediately with a volume of 6.1 and 12.2 mL that corresponds to 122 mg and 244 mg of DOXO-EMCH per vial. Filled trays are placed in a freeze dryer and freeze drying carried out according to the following lyophilization cycle:

| Temp (Celsius) | Time (hours) |
|---|---|
| −20 | 1:00 |
| −45 | 2:00 |
| −45 | 5:00 |
| −50 | 0:30 |
| Vacuum .1 mbar | |
| −25 | 2:00 |
| −25 | 23:00 |
| −25 | 23:00 |
| −25 | 4:00 |
| 20 | 2:00 |
| 20 | 20:00 |
| 20 | 10:00 |

Example 2

To a jacketed vessel fitted with an overhead stirrer are added 500 mL of a sterile 1:1 mixture of tert.-butanol and 20 mM sodium phosphate/10% sucrose, 1.2% N-acetyltryptophane (pH 6.0). The buffer mixture is stirred and with the aid of a circulating brine solution the temperature of the buffer is adjusted to 0° C. To the pre-cooled buffer mixture are added 10 g of the 6-maleimidocaproyl hydrazone derivative of doxorubicin hydrochloride (DOXO-EMCH HCl). DOXO-EMCH HCl is dissolved by stirring for 30 minutes and sterile-filtered through a Acropak filter (0.8/0.2 μm) into a second jacketed vessel set at −8° C. Under stirring 100 mL vials are filled immediately with a volume of 15 mL that corresponds to 300 mg of DOXO-EMCH per vial. Filled trays are placed in a freeze dryer and freeze drying carried out according to the following lyophilization cycle:

| Temp (Celsius) | Time (hours) |
|---|---|
| −20 | 1:00 |
| −45 | 2:00 |
| −45 | 5:00 |
| −50 | 0:30 |
| Vacuum .1 mbar | |
| −25 | 2:00 |
| −25 | 23:00 |
| −25 | 23:00 |
| −25 | 4:00 |
| 20 | 2:00 |
| 20 | 20:00 |
| 20 | 10:00 |

The invention claimed is:

1. A formulation comprising an anthracycline compound and an aromatic or heterocyclic compound, wherein the anthracycline compound has the general formula:

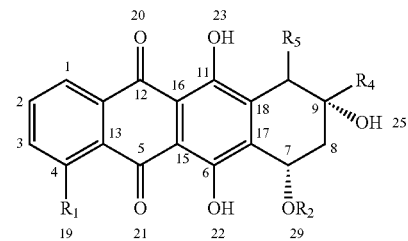

wherein $R_1$ is $OCH_3$, $OC_2H_5$, H or OH,
$R_2$ is a glycoside,
$R_4$ and $R_5$ independently are H, OH, $C_1$-$C_4$ alkyl, $OC_1$-$C_4$ alkyl or $C(CH_2R_3)$=N—NH—CO—X—Y,
wherein $R_3$ is H or OH, X is a linking group selected from the group consisting of —(CH$_2$)$_n$—, —(CH$_2$)$_n$—C$_6$H$_4$— and —C$_6$H$_4$—, wherein n=1-12, and Y is a binding group selected from the group consisting of a maleinimide group, a halogen acetate amide group, a halogen acetate group, a pyridyldithio group, an N-hydroxysuccinimide ester group, isothiocyanate group, a disulfide group, a vinylcarbonyl group, an aziridine group and an acetylene group, with the proviso that at least one of R$_4$ and R$_5$ is C(CH$_2$R$_3$)=N—NH—CO—X—Y, and wherein the aromatic or heterocyclic compound is an N-acetyl substituted amino acid selected from the group consisting of D-N-acetyltryptophan, L-N-acetyltryptophan, and D,L-N-acetyltryptophan.

2. The formulation of claim 1, wherein the anthracycline compound has the general formula

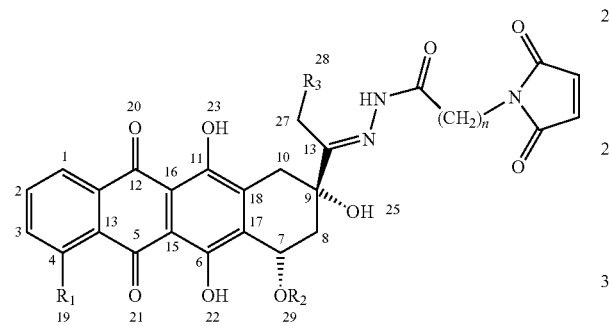

wherein
R$_1$ is OCH$_3$, H, OH, or OC$_2$H$_5$,
R$_2$ is a glycoside;
R$_3$ is H, OH or OCH$_3$, and
n is an integer from 1 to 12.

3. The formulation of claim 1, wherein the anthracycline compound is doxorubicin.

4. The formulation of claim 2, wherein n=5.

5. The formulation of claim 1, wherein the anthracycline compound is doxorubicin and n=5.

6. The formulation of claim 1 in which the anthracycline compound and the aromatic or heterocyclic compound is prepared as a pharmaceutically acceptable solution or lyophilized form.

7. The formulation of claim 1 further comprising tert-butanol and/or sucrose.

8. The formulation according to claim 6 or 7, wherein the formulation has been sterile-filtered.

9. A pharmaceutical composition suitable for the treatment of a cancer disease comprising the formulation of claim 1 and a pharmaceutically acceptable carrier or diluent.

10. A method to reduce aggregation and/or viscosity of a solution of anthracycline compounds comprising adding a compound selected from the group consisting of D-N-acetyltryptophane, L-N-acetyltryptophane, and D,L-N-acetyltryptophane to the solution.

11. The formulation of claim 2, wherein R$_2$ is 3-amino-2,3,6-trideoxy-alpha-L-lyxoheteropyranosyl, 3-amino-2,3,6-trideoxy-4-O-(tetrahydro-2H-pyran-3-yl)-alpha-L-lyxo-hexapyranosyl or 3-amino-2,3,6-trideoxy-4-O-(4-O-tetrahydro-2H-pyran-3-yl-tetrahydro-2H-pyran-3-yl)-alpha-L-lyxohexapyranosyl.

12. The formulation of claim 1, wherein

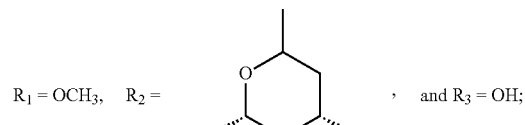

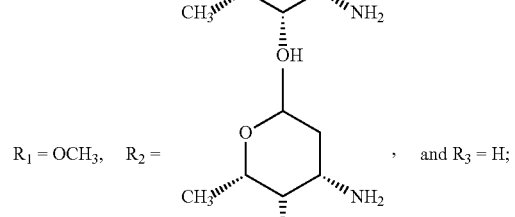

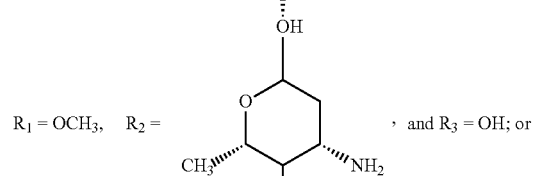

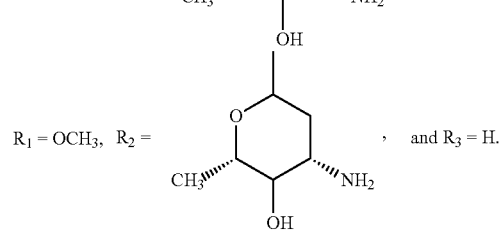

13. A formulation comprising an anthracycline compound and an aromatic or heterocyclic compound, wherein the anthracycline compound has the general formula:

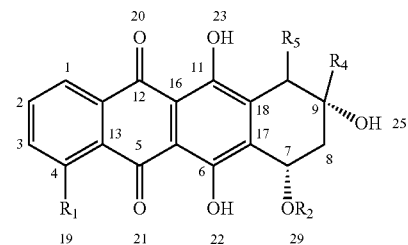

wherein R$_1$ is OCH$_3$, OC$_2$H$_5$, H or OH,
R$_2$ is a glycoside,
R$_4$ and R$_5$ independently are H, OH, C$_1$-C$_4$ alkyl, OC$_1$-C$_4$ alkyl or C(CH$_2$R$_3$)=N—NH—CO—X—Y,
wherein R$_3$ is H or OH,
X is a linking group selected from the group consisting of —(CH$_2$)$_n$—, —(CH$_2$)$_n$—C$_6$H$_4$— and —C$_6$H$_4$—, wherein n=1-12, and Y is a binding group selected from the group consisting of a maleinimide group, a halogen acetate amide group, a halogen acetate group, a pyridyldithio group, an N-hydroxysuccinimide ester group, isothiocyanate group, a disulfide group, a vinylcarbonyl group, an aziridine group and an acetylene group, with the proviso that at least one of R$_4$ and R$_5$ is C(CH$_2$R$_3$)=N—NH—CO—X—Y, and wherein the aromatic or heterocyclic compound is niacin, riboflavin or an N-acetyl substituted amino acid selected from the group consisting of tyrosine, phenylalanine, histidine or tryptophan.

* * * * *